US011702380B2

(12) United States Patent
Caille et al.

(10) Patent No.: US 11,702,380 B2
(45) Date of Patent: Jul. 18, 2023

(54) SYNTHESIS OF OMECAMTIV MECARBIL

(71) Applicant: Amgen Inc., Thousand Oaks, CA (US)

(72) Inventors: Sebastien Caille, Thousand Oaks, CA (US); James Murray, Newbury Park, CA (US); Kyle Quasdorf, Thousand Oaks, CA (US); Hannah Nguyen, Whittier, CA (US); Maria Victoria Silva Elipe, Thousand Oaks, CA (US); Ari Elizabeth Ericson, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 17/690,729

(22) Filed: Mar. 9, 2022

(65) Prior Publication Data

US 2022/0298099 A1 Sep. 22, 2022

Related U.S. Application Data

(60) Provisional application No. 63/159,227, filed on Mar. 10, 2021.

(51) Int. Cl.
C07C 201/08 (2006.01)

(52) U.S. Cl.
CPC .................. C07C 201/08 (2013.01)

(58) Field of Classification Search
CPC .... C07C 201/08; C07C 201/10; C07C 205/12
See application file for complete search history.

(56) References Cited

U.S. PATENT DOCUMENTS

| | | |
|---|---|---|
| 7,507,735 B2 | 3/2009 | Morgan et al. |
| 8,101,617 B2 | 1/2012 | Morgan et al. |
| 8,110,595 B2 | 2/2012 | Morgan et al. |
| 8,445,495 B2 | 5/2013 | Morgan et al. |
| 8,513,257 B2 | 8/2013 | Morgan et al. |
| 8,871,768 B2 | 10/2014 | Morgan et al. |
| 8,871,769 B2 | 10/2014 | Morgan et al. |
| 9,150,564 B2 | 10/2015 | Morgan et al. |
| 9,643,925 B2 | 5/2017 | Morgan et al. |
| 9,895,308 B2 | 2/2018 | Caldwell |
| 9,951,015 B2 | 4/2018 | Bi et al. |
| 9,988,354 B2 | 6/2018 | Cui et al. |
| 10,035,770 B2 | 7/2018 | Morgan et al. |
| 10,385,023 B2 | 8/2019 | Morgan et al. |
| 10,421,726 B2 | 9/2019 | Bi et al. |
| 10,543,215 B2 | 1/2020 | Scott et al. |
| 10,975,034 B2 | 4/2021 | Morgan et al. |
| 11,040,956 B2 | 6/2021 | Caille et al. |
| 11,384,053 B2 | 7/2022 | Bi et al. |
| 11,472,773 B2 | 10/2022 | Cui et al. |
| 2006/0014761 A1 | 1/2006 | Morgan et al. |
| 2007/0161617 A1 | 7/2007 | Morgan et al. |
| 2009/0036447 A1 | 2/2009 | Morgan et al. |
| 2009/0099198 A1 | 4/2009 | Morgan et al. |
| 2010/0029680 A1 | 2/2010 | Morgan et al. |
| 2012/0172372 A1 | 7/2012 | Morgan et al. |
| 2013/0324549 A1 | 12/2013 | Morgan et al. |
| 2014/0038983 A1 | 2/2014 | Morgan et al. |
| 2014/0309235 A1 | 10/2014 | Bi et al. |
| 2015/0005296 A1 | 1/2015 | Morgan et al. |
| 2016/0015628 A1 | 1/2016 | Caldwell |
| 2016/0016906 A1 | 1/2016 | Cui et al. |
| 2016/0115133 A1 | 4/2016 | Morgan et al. |
| 2017/0267638 A1 | 9/2017 | Morgan et al. |
| 2018/0140611 A1 | 5/2018 | Scott et al. |
| 2018/0273479 A1 | 9/2018 | Bi et al. |
| 2018/0305316 A1 | 10/2018 | Morgan et al. |
| 2018/0312469 A1 | 11/2018 | Cui et al. |
| 2019/0352267 A1 | 11/2019 | Morgan et al. |
| 2020/0079736 A1 | 3/2020 | Cui et al. |
| 2020/0108076 A1 | 4/2020 | Scott et al. |
| 2020/0155547 A1 | 5/2020 | Honarpour et al. |
| 2020/0277261 A1 | 9/2020 | Bi et al. |
| 2020/0308143 A1 | 10/2020 | Caille et al. |
| 2020/0331859 A1 | 10/2020 | Cui et al. |
| 2020/0399221 A1 | 12/2020 | Cui et al. |
| 2021/0198203 A1 | 7/2021 | Morgan et al. |
| 2021/0221771 A1 | 7/2021 | Morrison et al. |
| 2021/0292271 A1 | 9/2021 | Brasola et al. |
| 2021/0371397 A1 | 12/2021 | Caille et al. |
| 2022/0042055 A1 | 2/2022 | Bisagni et al. |
| 2022/0153700 A1 | 5/2022 | Cui et al. |
| 2022/0184068 A1 | 6/2022 | Honarpour et al. |
| 2022/0298114 A1 | 9/2022 | Bi et al. |

FOREIGN PATENT DOCUMENTS

| | | |
|---|---|---|
| CN | 101177400 A | 5/2008 |
| IN | 432022 A | 10/2022 |
| WO | 2014152270 A1 | 9/2014 |
| WO | 2019006231 A1 | 1/2019 |
| WO | 2020011626 A1 | 1/2020 |

(Continued)

OTHER PUBLICATIONS

U.S. Appl. No. 15/898,303, filed Feb. 16, 2018, by William Brett Caldwell et al. (U.S. Patent Application is not submitted herewith pursuant to the waiver of 37 C.F.R. § 1.98(a)(2)(iii) issued by the Office on Sep. 21, 2004.).

U.S. Appl. No. 17/176,003, filed Feb. 15, 2021, by Sheng Cui et al. (U.S. Patent Application is not submitted herewith pursuant to the waiver of 37 C.F.R. § 1,98(a)(2)(iii) issued by the Office on Sep. 21, 2004.).

U.S. Appl. No. 17/452,025, filed Oct. 22, 2021, by Bradley Paul Morgan et al. (U.S. Patent Application is not submitted herewith pursuant to the waiver of 37 C.F.R. § 1,98(a)(2)(iii) issued by the Office on Sep. 21, 2004.).

U.S. Appl. No. 17/454,592, filed Nov. 11, 2021, by Narimon Honarpour et al. (U.S. Patent Application is not submitted herewith pursuant to the waiver of 37 C.F.R. § 1,98(a)(2)(iii) issued by the Office on Sep. 21, 2004.).

Cantillo, D. et al. (Jan. 3, 2014). "A Scalable Procedure for Light-Induced Benzylic Brominations in Continuous Flow," The Journal of Organic Chemistry 79(1):223-229.

(Continued)

Primary Examiner — Jafar F Parsa
(74) Attorney, Agent, or Firm — Morrison & Foerster LLP

(57) ABSTRACT

Provided herein are synthetic methods for the preparation of intermediates that are utilized in the synthesis of omecamtiv mecarbil dihydrochloride.

59 Claims, 4 Drawing Sheets

(56) References Cited

FOREIGN PATENT DOCUMENTS

| WO | 2020014406 A1 | 1/2020 |
| WO | 2021053175 A1 | 3/2021 |
| WO | 2021053189 A1 | 3/2021 |
| WO | 2021070123 A1 | 4/2021 |
| WO | 2021070124 A1 | 4/2021 |
| WO | 2021136477 A1 | 7/2021 |
| WO | 2021163172 A1 | 8/2021 |
| WO | 2022192414 A2 | 9/2022 |

OTHER PUBLICATIONS

Dubost, E. et al. (Jul. 3, 2010, e-pub May 8, 2010). "General Method For The Synthesis Of Substituted Phenanthridin-6(5H)-ones Using a KOH-mediated Anionic Ring Closure As The Key Step," Tetrahedron, Elsevier Science Publishers, Amsterdam, NI, 66(27-28):5008-5016.

International Search Report and Written Opinion dated Sep. 29, 2022, for PCT Application No. PCT/US2022/019573, filed Mar. 9, 2022, 15 pages.

Invitation to Pay Additional Fees dated Jun. 23, 2022, for PCT Application No. PCT/US20202/019573, filed Mar. 9, 2022, 13 pages.

Jiang, M. et al. (Jan. 1, 2013). "Efficient Ipso-Nitration Of Arylboronic Acids With Iron Nitrate As The Nitro Source," RSC Advances 3(48):25602, 53 pages.

Murray, J.I. et al. (Feb. 18, 2022). "Ipso Nitration of Aryl Boronic Acids Using Fuming Nitric Acid," The Journal Of Organic Chemistry 87(4):1977-1985.

Murray, J.I. et al. (Aug. 21, 2020). "Kinetic Investigations to Enable Development of a Robust Radical Benzylic Bromination for Commercial Manufacturing of AMG 423 Dihydrochloride Hydrate," Organic Process Research & Development 24(8):1523-1530.

Quasdorf, K. et al. (Feb. 1, 2018). "Development of a Continuous Photochemical Bromination/Alkylation Sequence En Route to AMG 423," Organic Process Research and Development 26(2):458-466.

U.S. Appl. No. 17/798,531, filed Feb. 10, 2021, by Bi Mingda et al. br(A copy of the U.S. Patent Application is not submitted herewith pursuant to the waiver of 37 C.F.R. § 1.98(a)(2)(iii) issued by the Office dated Sep. 21, 2004.).

U.S. Appl. No. 17/929,645, filed Sep. 2, 2022, by Henry Morrison et al. br(A copy of the U.S. Patent Application is not submitted herewith pursuant to the waiver of 37 C.F.R. § 1.98(a)(2)(iii) issued by the Office dated Sep. 21, 2004.).

U.S. Appl. No. 17/930,695, filed Sep. 8, 2022, by Sheng Cui et al. br(A copy of the U.S. Patent Application is not submitted herewith pursuant to the waiver of 37 C.F.R. § 1.98(a)(2)(iii) issued by the Office dated Sep. 21, 2004.).

Process flow diagram (PFD) for LDA preparation

SYNTHESIS OF OMECAMTIV MECARBIL

CROSS-REFERENCE TO RELATED APPLICATIONS

This application claims priority to U.S. Provisional Application No. 63/159,227, filed Mar. 10, 2021, the disclosure of which is hereby incorporated by reference in its entirety for all purposes.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure and dilated cardiomyopathy (DCM) and conditions associated with left and/or right ventricular systolic dysfunction or systolic reserve. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

U.S. Pat. No. 7,507,735, herein incorporated by reference, discloses a genus of compounds, including omecamtiv mecarbil (AMG 423, CK-1827452) (herein "OM"), having the structure:

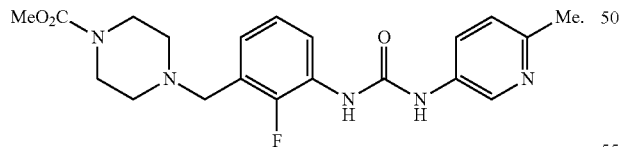

OM is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings. OM dihydrochloride hydrate is used in an oral formulation as a treatment of heart failure. Specific conditions include, but are not limited to, acute (or decompensated) congestive heart failure, and chronic congestive heart failure; particularly diseases associated with systolic heart dysfunction. Processes for the manufacture of OM are disclosed in WO 2014/152270 ("the '270 WO publication") and WO 2019/006231 ("the '231 WO publication").

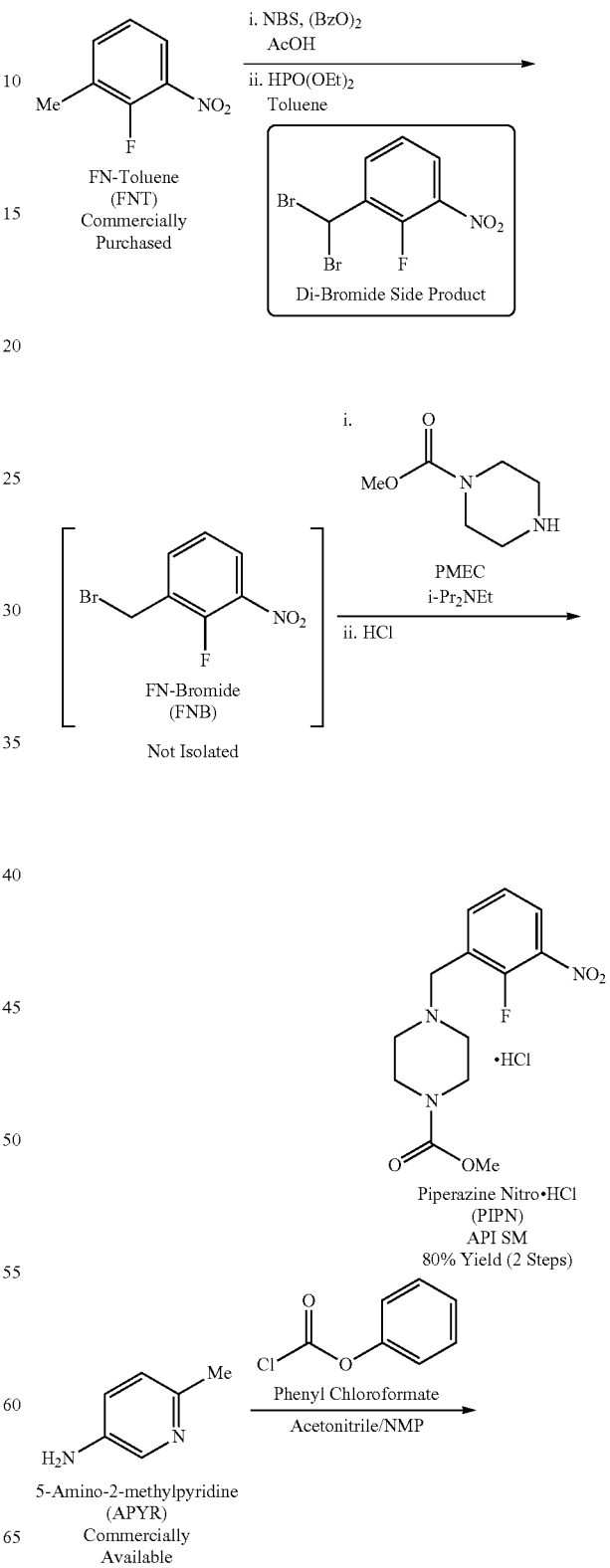

Scheme 1. WO 2014/152270 Process for OM

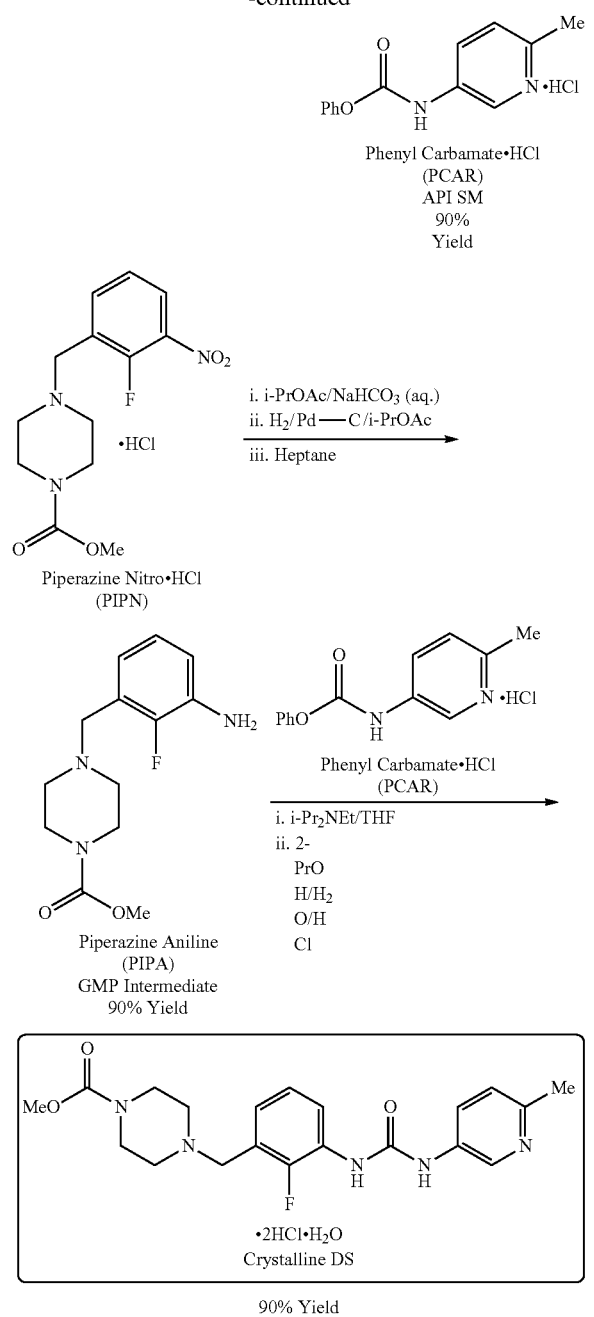

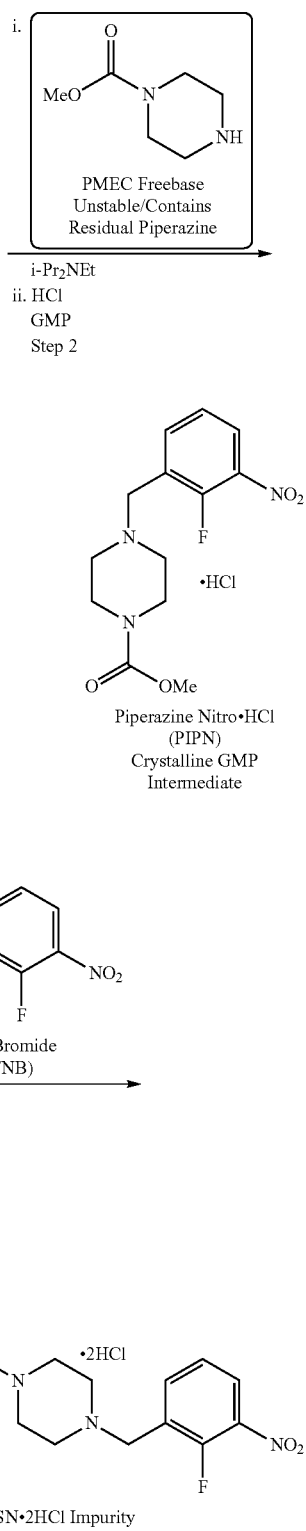

A process for preparing OM disclosed in WO 2014/152270 is summarized in Scheme 1. The process disclosed in the '270 WO publication comprises the preparation of regulatory API starting materials piperazine nitro (PIPN) HCl and phenyl carbamate (PCAR) HCl, from commercially available raw materials, 2-fluoro-3-nitrotoluene (FNT), and 5-amino-2-methylpyridine (APYR). PIPN is subsequently utilized with other advanced intermediate compounds to generate OM. The process of the '270 WO publication comprises using the intermediate PMEC free base. Although PMEC free base is commercially available as an oil, it contains various amounts of piperazine, which leads to the formation of the undesirable BISN impurity in the PIPN product, as shown in Scheme 2.

The process disclosed in the '231 WO publication describes a commercial process for preparing OM, including a process utilizing a stable crystalline salt of PMEC (i.e., PMEC phosphate hydrate) having low and constant levels of piperazine (Scheme 3).

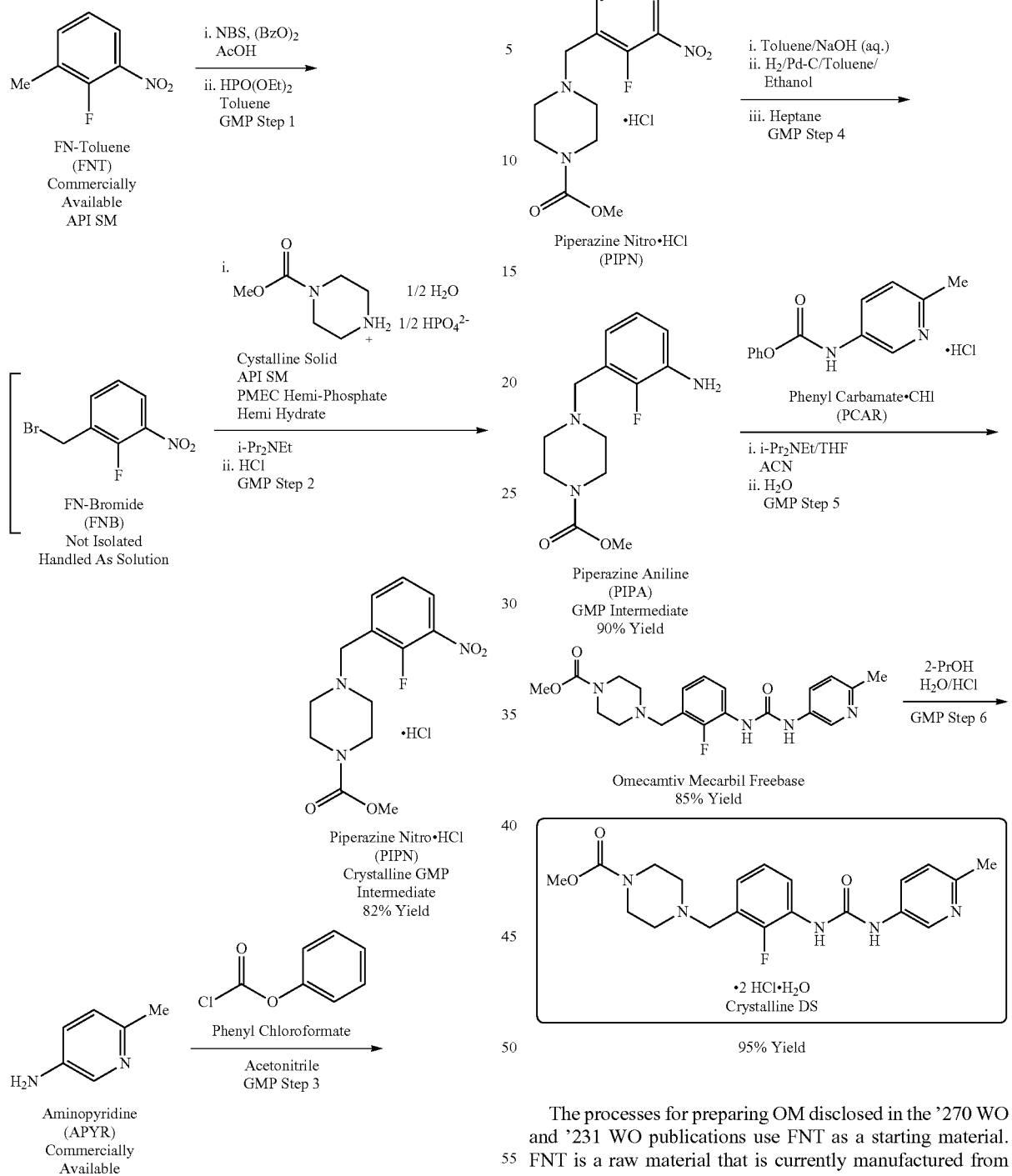

The processes for preparing OM disclosed in the '270 WO and '231 WO publications use FNT as a starting material. FNT is a raw material that is currently manufactured from 2-fluorotoluene using a short synthetic sequence. A drawback to this process is a requisite fractional distillation step of the mixture of isomers generated in order to afford the desired regioisomer, 2-fluoro-3-nitro-toluene, in acceptable purity, with no greater than 0.5% of any other isomers, as measured by gas chromatography. Moreover, the desired regioisomer of FNT is obtained by the process is less than 10% yield.

In view of the foregoing, there is a need for a reproducible, efficient preparation of FNT and other compounds useful for the manufacturing of OM.

SUMMARY

The disclosure provides processes for synthesizing 2-fluoro-3-nitrotoluene

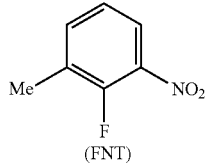

(FNT)

comprising (a) admixing 2-fluorotoluene with one or more bases and a boronation reagent to form a boronic acid and (b) admixing the resulting boronic acid with iron nitrate or a hydrate thereof to form FNT.

The disclosure also provides processes for synthesizing FNT comprising (a) admixing 2-fluorotoluene with one or more bases and a boronation reagent to form a boronic acid and (b) admixing the resulting boronic acid with nitric acid to form FNT.

The disclosure further provides a process for synthesizing 1-(bromomethyl)-2-fluoro-3-nitrobenzene

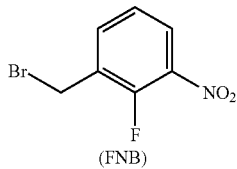

(FNB)

comprising
(a) admixing 2-fluoro-3-nitrotoluene (FNT) with a bromination agent in the presence of blue LED light to form a mixture of FNB and 1-(dibromomethyl)-2-fluoro-3-nitrobenzene

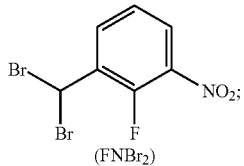

(FNBr$_2$)

(b) admixing the FNB/FNBr$_2$ mixture with a dialkyl phosphite to form FNB; and
(c) optionally purifying FNB formed in step (b) by (i) washing the FNB with a dialkylphosphite and a trialkylamine, or (ii) extracting the FNB with an organic solvent and washing with aqueous base.

DETAILED DESCRIPTION

Figure 1:
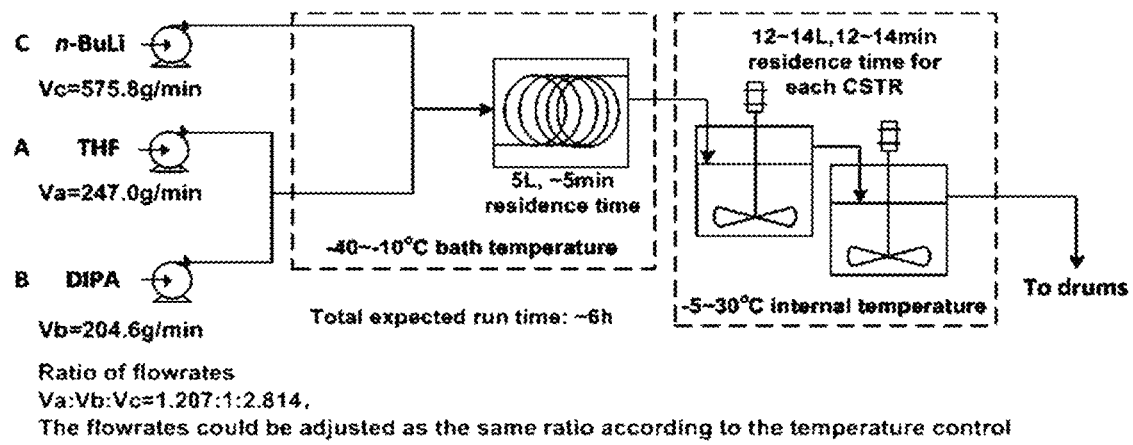
FIG. 1 shows the diagram for the set up for the flow chemistry preparation of LDA in Example 2-1.

Provided herein are processes for preparing FNT and other compounds useful in the manufacturing of OM and salts and hydrates thereof (e.g., OM dihydrochloride monohydrate). In some embodiments, the disclosure provides processes for manufacturing starting materials and intermediate compounds used in commercial processes for preparing OM dihydrochloride monohydrate.

In some embodiments, the disclosed processes are conducted in batch mode (i.e., "batch chemistry"). In other embodiments, the disclosed processes are conducted using continuous manufacturing processes (i.e., "flow chemistry" or "continuous chemistry"). As used herein, continuous manufacturing refers to an integrated system of unit operations, with constant flow (steady or periodic). The disclosed processes utilizing continuous chemistry can provide the production of gram to metric ton quantities of active pharmaceutical ingredients (APIs). In still other instances, the disclosed processes comprise a combination of steps that are conducted using batch chemistry and of steps conducted using continuous chemistry.

Processes for Synthesizing FNT

The disclosure provides processes for preparing FNT. In some embodiments, the processes for synthesizing FNT comprise (a) admixing 2-fluorotoluene with one or more bases and a boronation reagent to form a boronic acid and (b) admixing the resulting boronic acid with iron nitrate or a hydrate thereof to form FNT. Alternatively, in some embodiments, the disclosure provides processes for preparing FNT, wherein step (a) is as described above and step (b) is admixing the resulting boronic acid with nitric acid to form FNT. Illustrative embodiments of the process are shown in Scheme 4A and 4B, wherein the process depicted in Scheme 4A illustrates a batch process and the process depicted in Scheme 4B comprises a continuous manufacturing process (e.g., flow chemistry process).

Scheme 4A-B

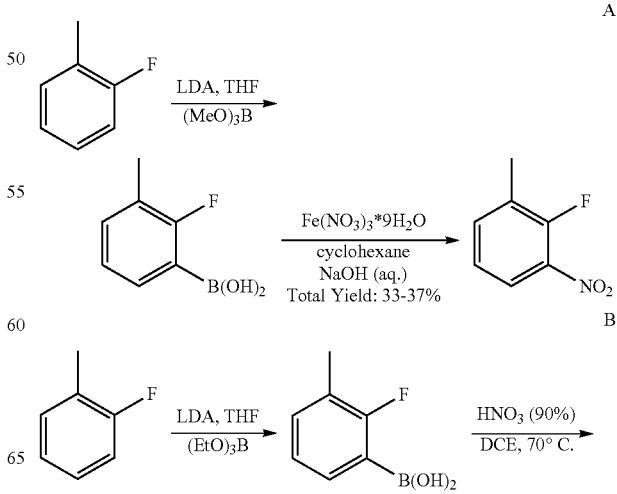

The disclosed processes provide a number of advantages over previous preparations of FNT from 2-fluorotoluene, which is a readily available and relatively inexpensive starting material. For example, the borylation reaction of 2-fluorotoluene facilitates an improved regioselectivity of the processes. The disclosed processes advantageously provide a selective nitration of 2-fluorotoluene offering a more regiospecific way to generate FNT with minimal byproducts when compared to previous methods thereby avoiding a fractional distillation step to obtain the desired regioisomer. In some embodiments, the FNT is further purified, for example, by simple distillation or crystallization (e.g., aqueous methanol). Further purification of FNT prepared by the disclosed processes is simplified since there are minimal byproducts (e.g., unwanted regioisomers).

In addition, the disclosed processes provide improved yields of FNT as compared to previous processes using 2-fluorotoluene as a starting material, which provide FNT in yields of only about 10%. In some embodiments, the disclosed processes provide FNT in a total yield from 2-fluorotoluene of greater than 10%, for example, 15%, 20%, 25%, 30%, 35%, or 40% or more.

Bases

The disclosed processes comprise using one or more bases in the borylation reaction (i.e., step (a)). Any suitable base can be employed in step (a), e.g., an organic base. In some embodiments, the one or more bases comprises lithium diisopropylamide (LDA), which can be formed by deprotonation of diisopropylamine (DIPA) by, e.g., n-butyl lithium.

In some embodiments, in conjunction with other above or below embodiments, the disclosed processes further comprise treating the product from step (b) with a second base. In these embodiments, the second base can comprise any suitable base capable of neutralizing any excess acid. Suitable second bases include, for example, alkaline hydroxides (e.g., lithium hydroxide, sodium hydroxide, potassium hydroxide, rubidium hydroxide, cesium hydroxide, magnesium hydroxide, calcium hydroxide, strontium hydroxide, barium hydroxide, tetramethylammonium hydroxide, and a combination thereof. In some embodiments, the second base comprises sodium hydroxide (NaOH) (e.g., an aqueous solution of NaOH).

Borylation Reaction

The disclosed processes for preparing FNT comprise a borylation reaction forming a boronic acid using a boronation reagent. The boronation reagent can be any suitable boronation reagent. Suitable boronation reagents include, for example, trialkyl borates. In some embodiments, the boronation reagent comprises trimethyl borate (MeO)$_3$B. In some embodiments, the boronation reagent comprises triethyl borate (EtO)$_3$B.

In some embodiments, in conjunction with other embodiments described herein, the LDA-borylation step is conducted as a flow chemistry step.

Solvents

In some embodiments, the processes disclosed herein are conducted in one or more suitable solvents. Illustrative suitable solvents include, for example, polar aprotic solvents, polar protic solvents, and non-polar solvents. Suitable polar aprotic solvents include, for example, tetrahydrofuran, 1,2-dichloroethane (DCE), acetonitrile (MeCN), and a mixture thereof. Suitable non-polar solvents include, for example, cyclohexane, pentanes, hexanes, benzene, toluene, diethyl ether, and a combination thereof. Suitable polar protic solvents include, for example, alcohols (e.g., methanol).

In some embodiments, in conjunction with other above or below embodiments, step (a) is carried out in a solvent comprising a polar aprotic solvent (e.g., tetrahydrofuran).

In conjunction with other above or below embodiments, in some embodiments step (b) is carried out in a solvent comprising a non-polar solvent (e.g., cyclohexane).

In some embodiments, in conjunction with other above or below embodiments, step (b) is carried out in a solvent comprising a polar aprotic solvent (e.g., DCE). In some embodiments wherein step (b) is carried out in DCE, DCE is present in an amount of 10 volumes to the boronic acid reagent.

In some embodiments, in conjunction with other above and below embodiments, the disclosed processes comprise a solvent switch wherein one or more additional solvents is introduced into a reaction vessel. In some embodiments, the one or more additional solvents substantially replaces a solvent that is present prior to the introduction of the one or more solvents. By way of example, in some embodiments of the nitration reaction disclosed herein, the nitration reaction is conducted in a solvent comprising 1,2-dichloroethane and during workup of the reaction, a solvent switch is conducted such that methanol is introduced to the organic phase.

Nitration Reaction

The disclosed processes for preparing FNT comprise nitrating a boronic acid to form FNT. In some embodiments, the disclosed processes comprise admixing a boronic acid with iron nitrate or a hydrate thereof to form FNT. In some embodiments, the iron nitrate is hydrated. In some embodiments, the iron nitrate has the formula Fe(NO$_3$)$_3$.XH$_2$O wherein X is an integer from 1-9. In some embodiments, the iron nitrate has the formula, Fe(NO$_3$)$_3$.9H$_2$O.

In some embodiments, in conjunction with other above or below embodiments, the disclosed processes comprise admixing a boronic acid with nitric acid to form FNT. In embodiments comprising nitration using nitric acid, the concentration of nitric acid can be any suitable concentration. In some embodiments, the concentration of nitric acid is 70% or greater aqueous (e.g., 80% or greater or 90% aqueous). In some embodiments, the disclosed processes comprise admixing the boronic acid with nitric acid while heating the reaction mixture. For example, the reaction is heated to 50° C. or greater (e.g., 55° C., 60° C., 65° C., 70° C., 75° C., or 80° C. or greater).

Furthermore, in some embodiments, in conjunction with other above or below embodiments, the reaction is heated for at least 8 hours. In some embodiments, the reaction is heated to 50° C. or greater for at least 8 hours. In some embodiments, the reaction is heated to 60° C. or greater for at least 8 hours. In some embodiments, the reaction is heated to 70° C. or greater for at least 8 hours. In some embodiments, the reaction is heated to 80° C. for at least 8 hours.

In various cases, the reaction is heated from 8 hours to 24 hours (e.g., 8, 9, 10, 11, 12, 13, 14, 15, 16, 17, 18, 19, 20, 21, 22, 23, or 24 hours). In some embodiments, the reaction is heated from 8 hours to 12 hours.

In some embodiments, in conjunction with other above or below embodiments, the process further comprises adding water to the reaction. For example, in some embodiments, 10 volumes of water, relative to the boronic acid reagent, are added. Moreover, in some embodiments the organic phase is washed with an aqueous solution of base (e.g., sodium bicarbonate). In addition, in some embodiments, one or more additional organic solvents are added (e.g., solvent switch) to facilitate isolation of the product.

In some embodiments, the solvent is removed using distillation (e.g., vacuum distillation under reduced pressure). By way of example, in some embodiments the solvent comprising 1,2-dichloroethane is removed by vacuum distillation at reduced pressure (e.g., 35 Torr).

The crude FNT is purified using any suitable technique. In some embodiments, in conjunction with other above or below embodiments, the FNT is crystallized from methanol/water. In some embodiments, in conjunction with other above or below embodiments, the FNT is purified by fractional distillation at 110-120° C.

In some embodiments, in conjunction with other embodiments described herein, the nitration reaction is conducted in batch-mode subsequent to the borylation reaction conducted using a continuous manufacturing process.

Compounds Useful for Preparing OM

In various embodiments, the disclosure provides processes for preparing intermediate compounds useful for preparing OM (e.g., FNT, FNB, PIPN or a salt thereof, PMEC, PCAR, and/or PIPA), wherein the synthesis of the intermediate compounds comprises using FNT. In some embodiments, the FNT is prepared according to the processes described herein.

FNB

In some embodiments, the disclosure provides a process for synthesizing 1-(bromomethyl)-2-fluoro-3-nitrobenzene:

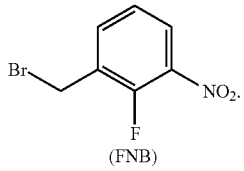

(FNB)

In various embodiments, in conjunction with other above or below embodiments, the disclosed processes for synthesizing FNB comprise admixing FNT with a bromination agent in the presence of blue LED light to form a mixture of FNB and the dibrominated compound, 1-(dibromomethyl)-2-fluoro-3-nitrobenzene

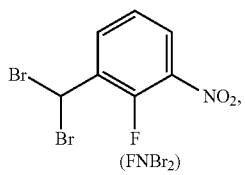

(FNBr2)

wherein the FNB/FNBr2 mixture is admixed with a dialkyl phosphite to form FNB.

As used herein, "blue LED light" refers to light emitted at a wavelength of 400 nm to 460 nm (e.g., 435-445 nm). An illustrative blue LED light is commercially available from MilliporeSigma (St. Louis, Mo.) having a LED light ring (IP68) with wavelength of 435-445 nm.

In some embodiments, the disclosed process further comprises further purifying the FNB, for example, by further washing and/or extraction processes. By way of example, in some embodiments, FNB is further purified by washing the FNB with a dialkylphosphite and a trialkylamine base or by extracting the FNB with an organic solvent and washing with aqueous base. In some embodiments, the FNB the organic solvent is toluene. In some embodiments, the aqueous base is aqueous sodium hydroxide.

In various embodiments, the FNT used to prepare FNB is prepared according to the processes disclosed herein.

The bromination agent can be any suitable bromination agent. In some embodiments, the bromination agent is N-bromosuccinimide (NBS).

The dialkyl phosphite can be any suitable dialkyl phosphite. In some embodiments, the dialkyl phosphite is selected from the group consisting of dimethyl phosphite, diethyl phosphite, and a combination thereof. In some embodiments, the dialkyl phosphite is diethyl phosphite.

In various embodiments, the disclosed processes for preparing FNB further comprise converting FNB into other compounds suitable for preparing omecamtiv mecarbil.

PIPN or Salts Thereof

In some embodiments, the disclosure provides processes for preparing methyl 4-(2-fluoro-3-nitrobenzyl)piperazine-1-carboxylate

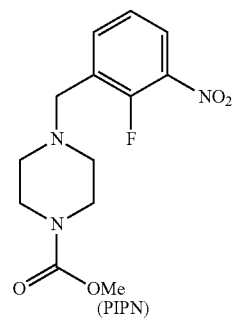

(PIPN)

or a salt thereof. Illustrative salts of PIPN include a hydrobromide, a hydrochloride, and a mixture thereof. In some embodiments, PIPN is prepared and/or isolated as the hydrobromide salt.

PIPN—Photochemical Bromination

In some embodiments, the disclosure provides processes for preparing PIPN or a salt thereof comprising a photochemical bromination reaction. For example, the disclosure provides processes for synthesizing PIPN or a salt thereof from FNB prepared according to the photochemical processes described herein. In various embodiments, the processes comprise admixing FNB, a trialkylamine base, and piperazine methyl carboxylate

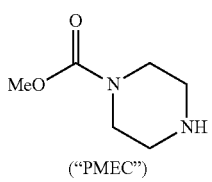

("PMEC")

phosphate hydrate to form PIPN or a salt thereof.

As used herein, the trialkylamine base can be any suitable trialkylamine base. Illustrative suitable trialkylamine bases include, for example, diisopropylethylamine (i.e., Hunig's base), trimethylamine, and a mixture thereof.

PIPN—Free Radical Bromination

In some embodiments, the disclosure provides processes for preparing PIPN or a salt thereof from FNT obtained as described herein, wherein the bromination reaction is a free radical bromination. For example, in some embodiments, the disclosed processes comprise admixing FNT, benzoyl peroxide, NBS, and acetic acid at a temperature of 70-95° C. to form FNB; optionally extracting FNB with toluene, washing FNB with an aqueous basic solution, or both; and admixing FNB, a trialkylamine base, and PMEC phosphate hydrate to form PIPN or a salt thereof.

In some embodiments, in conjunction with other above or below embodiments, the processes further comprise purifying the FNB that is formed prior to conducting further conversions. For example, in some embodiments, the processes further comprise extracting the FNB formed with toluene and washing with aqueous sodium hydroxide prior to admixing with a trialkylamine base and PMEC phosphate hydrate. Further, in some embodiments, the processes further comprise washing the FNB that is formed with aqueous sodium thiosulfate and aqueous sodium chloride prior to admixing with a trialkylamine base and PMEC phosphate hydrate.

Regardless whether the bromination reaction is catalyzed by a photochemical process or free radical process, it is desirable to minimize the amount of $FNBr_2$ that is formed. In some embodiments, in conjunction with other above or below embodiments, prior to admixing the FNB, the trialkylamine base, and PMEC phosphate hydrate, the process further comprises adding a dialkyl phosphite (e.g., diethylphosphite) and a trialkylamine base, and admixing the resulting mixture at a temperature of 30-65° C.

In some embodiments, in conjunction with other above or below embodiments, the disclosure provides continuous manufacturing processes for producing PIPN.HBr utilizing PMEC phosphate as shown in Scheme 5.

Scheme 5

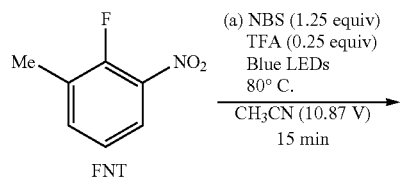

(a) NBS (1.25 equiv)
TFA (0.25 equiv)
Blue LEDs
80° C.
$CH_3CN$ (10.87 V)
15 min

FNT

-continued

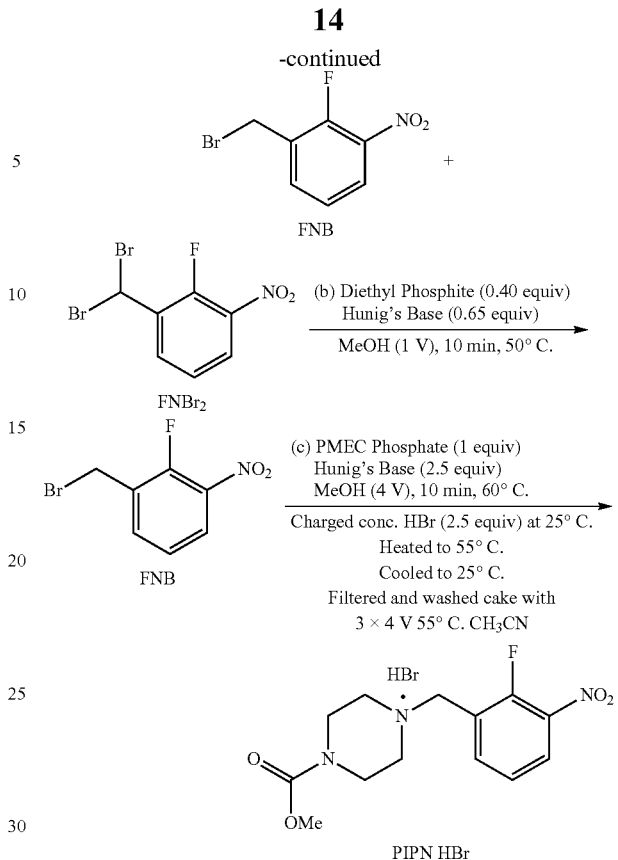

As shown in Scheme 5, PIPN is isolated as the hydrobromide salt. This is in contrast to prior syntheses which isolated PIPN as the hydrochloride salt, inevitably leading to mixtures of PIPN hydrobromide and PIPN hydrochloride. Thus, utilizing HBr instead of HCl to generate the corresponding PIPN salt provides solely the PIPN HBr salt which can be utilized as easily and effectively in the downstream synthetic pathway. The flow process of preparing PIPN HBr (as opposed to the batch process utilized to prepare PIPN HCl) provides for the synthesis of the same required intermediate while also reducing the number of unit operations.

In some embodiments, step (a) is admixed in the presence of a polar aprotic solvent (e.g., acetonitrile), as described herein. In certain embodiments, step (a) is admixed in the presence of an acid. Illustrative suitable acids include, for example, acetic acid, trifluoroacetic acid (TFA), and a mixture thereof.

In some embodiments, in conjunction with other above or below embodiments, step (a) is heated (e.g., heated to at least 80° C., or to 80° C. to 120° C., or to 80° C. to 100° C.). In some embodiments, step (a) is heated for a period of time, for example 5 to 20 minutes (e.g., 5, 6, 7, 8, 9, 10, 11, 12, 13, 14, 15, 16, 17, 18, 19, or 20 minutes). In some embodiments, step (a) is heated to 80° C. for 15 minutes.

In some embodiments, step (b) and/or step (c) are admixed in the presence of a polar protic solvent (e.g., MeOH), as described herein. In some embodiments, step (b) is admixed in the presence of a base (e.g., a trialkylamine base). In some embodiments, the trialkylamine is diisopropylethylamine (Hunig's base).

In certain embodiments, step (b) is heated (e.g., heated to 50° C., or to 50° C. to 80° C., or to 50° C. to 60° C.). In some embodiments, step (b) is heated to 50° C. for 10 minutes.

In some embodiments, step (c) is heated (e.g., heated to 60° C., or to 60° C. to 90° C., or to 60° C. to 70° C.). In some embodiments, step (c) is heated to 60° C. for 10 minutes.

In some embodiments, prior to admixing the FNB, a base, and PMEC phosphate hydrate of step (c), the process further comprises adding diethylphosphite and a trialkylamine base, and admixing the resulting mixture at a temperature of 30-65° C.

PMEC

The disclosed processes for preparing PIPN or a salt thereof comprise using PMEC phosphate hydrate. In various embodiments, the PMEC phosphate hydrate is prepared by a process comprising (a) admixing piperazine and methyl chloroformate to form PMEC; (b) admixing the PMEC and 0.5 molar equivalents of phosphoric acid to form PMEC phosphate hydrate; and (c) optionally filtering the PMEC phosphate hydrate from the admixture of step (b).

In some embodiments, step (a) is performed in an aqueous solution and/or step (a) is performed at a temperature of 20-55° C. for a period of time (e.g., 1-12 h).

In some embodiments, in conjunction with other above or below embodiments, the disclosed processes for preparing PIPN or a salt thereof, further comprise isolating the PMEC formed from step (a) as a solution in a solvent selected from methylene chloride, dichloroethane, 2-methyltetrahydrofuran, and a mixture thereof. In some embodiments, the PMEC is isolated by (i) washing the resulting PMEC from step (a) with an organic solvent; (ii) modifying the pH to 8 to 14 by adding a base to form a basic aqueous solution; and (iii) extracting the PMEC from the basic aqueous solution of step (ii) with methylene chloride, dichloroethane, 2-methyl tetrahydrofuran, or a mixture thereof.

PIPA

In some embodiments, the disclosure provides processes for preparing methyl 4-(3-amino-2-fluorobenzyl)piperazine-1-carboxylate (PIPA):

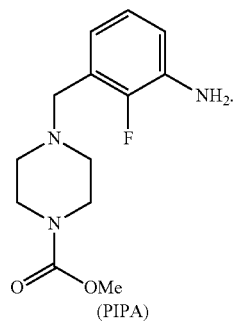

(PIPA)

In various embodiments, the disclosure provides processes for preparing PIPA from PIPN or a salt thereof that is obtained according to the disclosed processes. In some embodiments, the disclosure provides processes for synthesizing PIPA comprising (a) admixing PIPN or a salt thereof, an aqueous solution of an inorganic base, and toluene to form a PIPN freebase solution; (b) hydrogenating the PIPN freebase solution in the presence of a palladium catalyst in a solvent comprising toluene and alcohol solvent mixture to form crude PIPA, wherein the alcohol comprises ethanol or isopropanol; and (c) crystallizing the PIPA from the crude PIPA in heptane and toluene.

In some embodiments, the inorganic base comprises sodium hydroxide.

PCAR, APYR, & NPYR

In some embodiments, the disclosure provides processes for phenyl (6-methylpyridin-3-yl) carbamate

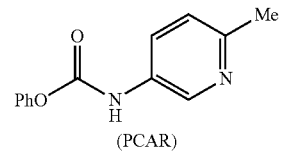

(PCAR)

or a salt thereof (e.g., PCAR hydrochloride). The disclosed processes comprise admixing 5-amino-2-methylpyridine

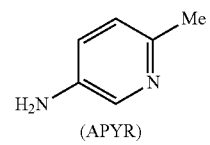

(APYR)

and phenyl chloroformate in acetonitrile to form PCAR or a salt thereof, wherein the admixing is performed in the absence of N-methyl-2-pyrrolidinone (NMP). In some embodiments, the PCAR is formed as a hydrochloride salt.

In some embodiments, the admixing is performed at a temperature of 15-30° C. for 1 to 15 hours.

In conjunction with other above or below embodiments, in some embodiments the disclosed processes for synthesizing PCAR or a salt thereof, further comprise, prior to admixing APYR and phenyl chloroformate, purifying APYR by a process comprising (i) washing an isopropyl acetate solution of crude APYR, wherein the crude APYR comprises up to 10 wt % APYR hydrochloride, with aqueous sodium hydroxide, and admixing the washed APYR with charcoal to form an APYR solution after filtration; and (ii) crystallizing APYR from the APYR solution of step (i) from isopropyl acetate and heptane.

In some embodiments, in conjunction with other above or below embodiments, the APYR is prepared by a process comprising (i) hydrogenating 2-methyl-5-nitropyridine (NPYR)

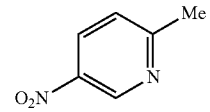

in the presence of a palladium catalyst to form crude APYR; and (ii) crystallizing the crude APYR from isopropyl acetate and heptane.

In some embodiments, the NPYR is washed in isopropyl acetate with aqueous sodium hydroxide, followed by admixing the washed NPYR in isopropyl acetate with charcoal, prior to step (i).

In some embodiments, in conjunction with other above or below embodiments, the disclosed processes further comprise comprising crystallizing PCAR.

OM

The disclosure provides processes for preparing OM (e.g., omecamtiv mecarbil dihydrohchloride monohydrate; "OM 2HCl H₂O") from one or more intermediate compounds (e.g., FNT, FNB, PIPN or a salt thereof, PIPA, PCAR, APYR, and/or NPYR) obtained from the processes disclosed herein.

In some embodiments, the disclosed processes for preparing OM dihydrochloride monohydrate comprise (a) admixing PIPA, PCAR, and a trialkylamine base in acetonitrile and tetrahydrofuran to form a solution of crude OM; (b) isolating OM free base from the solution of crude OM; and (c) admixing the isolated OM free base with 2 to 3 molar equivalents of hydrochloric acid in isopropanol and water to form OM dihydrochloride monohydrate.

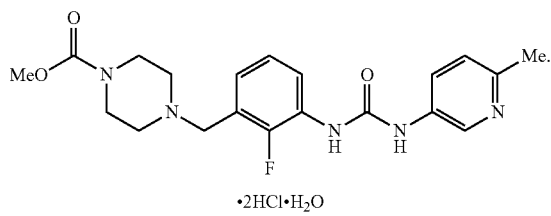 [SMILES: COC(=O)N1CCN(Cc2cccc(NC(=O)Nc3ccc(C)nc3)c2F)CC1]

·2HCl·H₂O

The trialkylamine base is any suitable trialkylamine base, as described herein.

In some embodiments, the isolating of step (b) comprises crystallizing omecamtiv mecarbil free base by adding water to the solution of crude omecamtiv mecarbil from step (a) and filtering the crystallized omecamtiv mecarbil free base.

In some embodiments, the disclosed processes further comprise comprising crystallizing the omecamtiv mecarbil dihydrochloride monohydrate from isopropanol and water.

In some embodiments, in conjunction with other above or below embodiments, the PCAR is prepared according to the processes disclosed herein.

In some embodiments, the disclosure provides processed for preparing omecamtiv mecarbil dihydrochloride monohydrate comprising (a) admixing PIPA, triphosgene, and a trialkylamine in acetonitrile and tetrahydrofuran to form PIPA isocyanate; (b) admixing the PIPA isocyanate and APYR to form OM free base, (c) admixing the OM free base with 2 to 3 molar equivalents of hydrochloric acid in isopropanol and water to form OM dihydrochloride monohydrate.

In some embodiments, step (a) is performed via continuous manufacturing comprising admixing a first solution comprising PIPA and the trialkylamine in acetonitrile and a second solution comprising triphosgene in tetrahydrofuran using a micromixer chip and a reaction loop to form the PIPA isocyanate.

In some embodiments, in conjunction with other above or below embodiments, step (b) is performed via continuous manufacturing comprising admixing a solution comprising the PIPA isocyanate and a solution comprising the AYPR using a Y-mixer and a reaction loop.

A number of processes disclosed herein include steps noted as optional. In some cases, the optional step is not performed. In other cases, the optional step is performed.

EMBODIMENTS

1. A process for synthesizing 2-fluoro-3-nitrotoluene ("FNT") comprising
   (a) admixing 2-fluorotoluene with one or more bases and a boronation reagent to form a boronic acid; and
   (b) admixing the resulting boronic acid with iron nitrate or a hydrate thereof to form the FNT.
2. The process of embodiment 1, wherein the one or more bases comprises lithium diisopropylamide (LDA).
3. The process of embodiment 2, wherein the LDA is added in the presence of diisopropylamine (DIPA).
4. The process of any one of embodiments 1-3, wherein step (a) is carried out in a polar aprotic solvent.
5. The process of embodiment 4, wherein the polar aprotic solvent comprises tetrahydrofuran (THF).
6. The process of any one of embodiments 1-5, wherein step (b) is carried out in a non-polar solvent.
7. The process of embodiment 6, wherein the non-polar solvent comprises cyclohexane.
8. The process of any one of embodiments 1-7, wherein the iron nitrate is hydrated.
9. The process of embodiment 8, wherein the iron nitrate has the formula, $Fe(NO_3)_3 \cdot 9H_2O$.
10. The process of any one of embodiments 1-9, further comprising treating the product from step (b) with a second base.
11. A process for synthesizing 2-fluoro-3-nitrotoluene ("FNT") comprising
    (a) admixing 2-fluorotoluene with one or more bases and a boronation reagent to form a boronic acid; and
    (b) admixing the resulting boronic acid with nitric acid to form the FNT.
12. The process of embodiment 11, wherein the one or more bases comprises lithium diisopropylamide (LDA).
13. The process of embodiment 12, wherein the LDA is added in the presence of diisopropylamine (DIPA).
14. The process of any one of embodiments 11-13, wherein step (a) is carried out in a polar aprotic solvent.
15. The process of embodiment 14, wherein the polar aprotic solvent comprises tetrahydrofuran (THF).
16. The process of any one of embodiments 11-15, wherein step (b) is carried out in a polar aprotic solvent.
17. The process of embodiment 16, wherein the polar aprotic solvent comprises 1,2-dichloroethane (DCE).
18. The process of embodiment 17, wherein the DCE is present as 10 volumes to the boronation reagent.
19. The process of any one of embodiments 11-18, wherein the nitric acid is 90% aqueous.
20. The process of any one of embodiments 11-19, wherein the process further comprises heating the admixture formed in step (b).
21. The process of embodiment 20, wherein the admixture is heated for no less than 8 hours.
22. The process of embodiment 20 or 21, wherein the admixture is heated to 70° C. for no less than 8 hours.
23. The process of any one of embodiments 11-22, further comprising adding water to the admixture formed in step (b).
24. The process of embodiment 23, wherein 10 volumes of water are added relative to the boronation reagent.
25. A process for synthesizing 1-(bromomethyl)-2-fluoro-3-nitrobenzene comprising
(a) admixing 2-fluoro-3-nitrotoluene (FNT) with a bromination agent in the presence of blue LED light to form a mixture of FNB and 1-(dibromomethyl)-2-fluoro-3-nitrobenzene

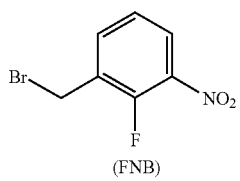
(FNB)

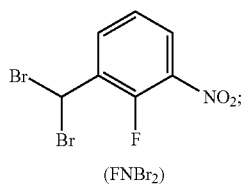
(FNBr₂)

(b) admixing the FNB/FNBr₂ mixture with a dialkyl phosphite to form FNB; and
(c) optionally purifying FNB formed in step (b) by (i) washing the FNB with a dialkylphosphite and a trialkylamine, or (ii) extracting the FNB with an organic solvent and washing with aqueous base.

26. The process of embodiment 25, wherein the FNT is prepared by a process of any one of embodiments 1-24.
27. The process of embodiment 25 or 26, wherein the organic solvent is toluene.
28. The process of any one of embodiments 25-27, wherein the base is sodium hydroxide.
29. The process of any one of embodiments 25-28, wherein the bromination agent is selected from N-bromosuccinimide.
30. The process of any one of embodiments 25-29, wherein the dialkyl phosphite is selected from the group consisting of dimethylphosphite, diethylphosphite, and a combination thereof.
31. The process of any one of embodiments 25-30, further comprising
(d) admixing the FNB, a trialkylamine base, and piperazine methyl carboxylate

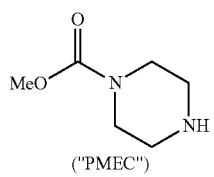
("PMEC")

phosphate hydrate to form methyl 4-(2-fluoro-3-nitrobenzyl)piperazine-1-carboxylate

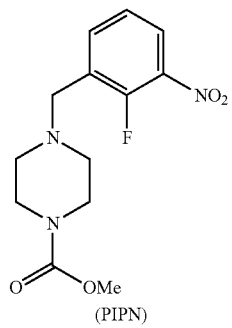
(PIPN)

or a salt thereof.
32. The process of any one of embodiments 1-24, further comprising
(c) admixing the FNT, benzoyl peroxide, N-bromosuccinimide, and acetic acid at a temperature of 70 to 95° C. to form 1-(bromomethyl)-2-fluoro-3-nitrobenzene

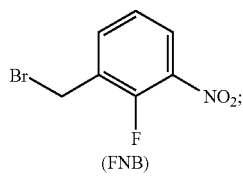
(FNB)

(d) optionally extracting FNB with toluene, washing FNB with an aqueous basic solution, or both;
(e) admixing FNB, a trialkylamine base, and piperazine methyl carboxylate

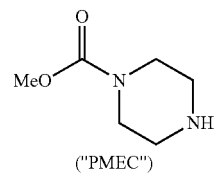
("PMEC")

phosphate hydrate to form methyl 4-(2-fluoro-3-nitrobenzyl)piperazine-1-carboxylate

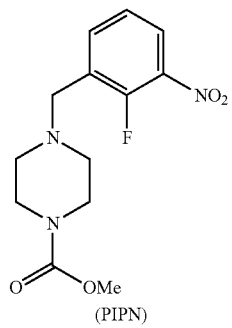
(PIPN)

or a salt thereof.
33. The process of embodiment 32, wherein FNB is extracted with toluene and washed with aqueous sodium hydroxide prior to step (e).
34. The process of any one of embodiments 31-33, wherein the PIPN is formed as a hydrobromide salt.

35. The process of any one of embodiments 31-34, wherein the PMEC phosphate hydrate is prepared by a process comprising
   (a) admixing piperazine and methyl chloroformate to form PMEC;
   (b) admixing the PMEC and 0.5 molar equivalents of phosphoric acid to form PMEC phosphate hydrate; and
   (c) optionally filtering the PMEC phosphate hydrate from the admixture of step (b).
36. The process of embodiment 35, further comprising isolating the PMEC formed from step (a) as a solution in a solvent selected from methylene chloride, dichloroethane, 2-methyltetrahydrofuran, and a mixture thereof.
37. The process of embodiment 36, wherein the isolating is performed by
   (i) washing the resulting PMEC from step (a) with an organic solvent;
   (ii) modifying the pH to 8 to 14 by adding a base to form a basic aqueous solution; and
   (iii) extracting the PMEC from the basic aqueous solution of step (ii) with methylene chloride, dichloroethane, 2-methyl tetrahydrofuran, or a mixture thereof.
38. The process of any one of embodiments 35-37, wherein step (a) is performed in an aqueous solution.
39. The process of any one of embodiments 35-38, wherein step (a) is performed at a temperature of 20 to 55° C. for 1 to 12 hours.
40. The process of any one of embodiments 31-39, wherein the trialkylamine base comprises diisopropylethylamine or triethylamine.
41. The process of any one of embodiments 31-40, wherein prior to admixing the FNB, the trialkylamine base, and the PMEC phosphate hydrate, the process further comprises adding diethylphosphite and a trialkylamine base, and admixing the resulting mixture at a temperature of 30 to 65° C.
42. The process of any one of embodiments 31-41, further comprising
   (f) admixing the PIPN or salt thereof, an aqueous solution of an inorganic base, and toluene to form a PIPN freebase solution;
   (g) hydrogenating the PIPN freebase solution in the presence of a palladium catalyst in a solvent comprising toluene and alcohol to form crude methyl 4-(3-amino-2-fluorobenzyl)piperazine-1-carboxylate (PIPA):

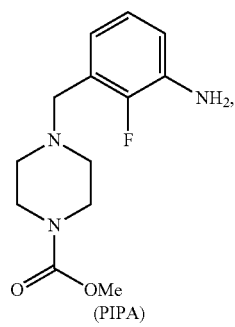 [SMILES: COC(=O)N1CCN(Cc2cccc(N)c2F)CC1]
(PIPA)

wherein the alcohol comprises ethanol or isopropanol; and
   (h) crystallizing the PIPA from the crude PIPA in heptane and toluene.
43. The process of embodiment 42, wherein the inorganic base comprises sodium hydroxide.

44. The process of embodiment 42 or 43, further comprising
   (i) admixing the PIPA, phenyl (6-methylpyridin-3-yl) carbamate

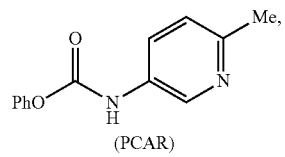 [SMILES: Cc1ccc(NC(=O)Oc2ccccc2)cn1]
(PCAR)

and a trialkylamine base in acetonitrile and tetrahydrofuran to form a solution of crude omecamtiv mecarbil;
   (j) isolating omecamtiv mecarbil free base from the solution of crude omecamtiv mecarbil; and
   (k) admixing the isolated omecamtiv mecarbil free base with 2 to 3 molar equivalents of hydrochloric acid in isopropanol and water to form omecamtiv mecarbil dihydrochloride hydrate

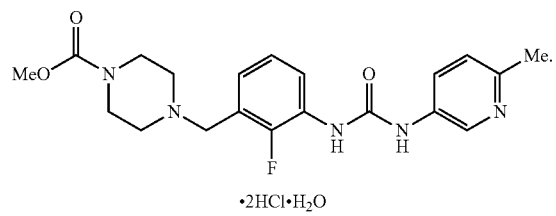 [SMILES: COC(=O)N1CCN(Cc2cccc(NC(=O)Nc3ccc(C)nc3)c2F)CC1]
·2HCl·H$_2$O

45. The process of embodiment 44, wherein the trialkylamine base comprises diisopropylethylamine or triethylamine.
46. The process of embodiment 44 or 45, wherein the isolating of step (h) comprises crystallizing omecamtiv mecarbil free base by adding water to the solution of crude omecamtiv mecarbil from step (g) and filtering the crystallized omecamtiv mecarbil free base.
47. The process of any one of embodiments 44-46, further comprising crystallizing the omecamtiv mecarbil dihydrochloride hydrate from isopropanol and water.
48. The process of any one of embodiments 44-47, wherein the PCAR or a salt thereof is prepared by a process comprising
   admixing 5-amino-2-methylpyridine

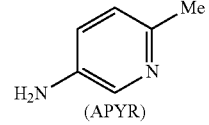
(APYR)

and phenyl chloroformate in acetonitrile to form PCAR or a salt thereof, wherein the admixing is performed in the absence of N-methyl 2-pyrrolidinone (NMP).
49. The process of embodiment 48, wherein the admixing is performed at a temperature of 15 to 30° C. for 1 to 15 hours.
50. The process of embodiment 48 or 49, wherein the PCAR is formed as a hydrochloride salt.

51. The process of any one of embodiments 48-50, wherein the APYR is prepared by a process comprising
   (i) hydrogenating 2-methyl-5-nitropyridine

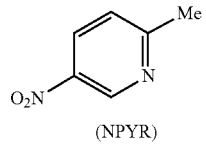

(NPYR)

in the presence of a palladium catalyst to form crude APYR; and
   (ii) crystallizing the crude from isopropyl acetate and heptane.
52. The process of embodiment 51, further comprising, prior to step (i), washing NPYR in isopropyl acetate with aqueous sodium hydroxide, followed by admixing the washed NPYR in isopropyl acetate with charcoal.
53. The process of any one of embodiments 48-52, further comprising, prior to admixing APYR and phenyl chloroformate, purifying APYR by a process comprising:
   (i) washing an isopropyl acetate solution of crude APYR, wherein the crude APYR comprises up to 10 wt % APYR hydrochloride, with aqueous sodium hydroxide, and admixing the washed APYR with charcoal to form an APYR solution after filtration; and
   (ii) crystallizing APYR from the APYR solution of step (i) from isopropyl acetate and heptane.
54. The process of any one of embodiments 48-53, further comprising crystallizing PCAR.
55. The process of embodiment 42 or 43, further comprising
   (i) admixing the PIPA, triphosgene, and a trialkylamine in acetonitrile and tetrahydrofuran to form PIPA isocyanate;
   (j) admixing the PIPA isocyanate and 5-amino-2-methylpyridine

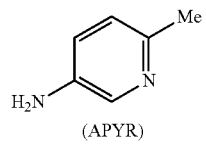

(APYR)

to form omecamtiv mecarbil free base; and
   (k) admixing the omecamtiv mecarbil free base with 2 to 3 molar equivalents of hydrochloric acid in isopropanol and water to form omecamtiv mecarbil dihydrochloride hydrate.
56. The process of embodiment 55, wherein step (g) is performed via continuous manufacturing comprising admixing a first solution comprising PIPA and the trialkylamine in acetonitrile and a second solution comprising triphosgene in tetrahydrofuran using a micromixer chip and a reaction loop to form the PIPA isocyanate.
57. The process of embodiment 55 or 56, wherein step (h) is performed via continuous manufacturing comprising admixing a solution comprising the PIPA isocyanate and a solution comprising the AYPR using a Y-mixer and a reaction loop.
58. A process for preparing omecamtiv mecarbil or a salt thereof, a hydrate thereof, or a salt hydrate thereof, the process comprising the process of any one of embodiments 1-43.

59. The process of embodiment 58, wherein the omecamtiv mecarbil, salt thereof, hydrate thereof, or salt hydrate thereof is omecamtiv mecarbil dihydrochloride hydrate.

EXAMPLES

The following examples further illustrate the disclosed methods of treatment, but of course, should not be construed as in any way limiting its scope.

The following abbreviations are used in the Examples: PFR refers to plug flow reactor; CSTR refers to continuous stirred tank reactor; MTBE refers to methyl tent-butyl ether; NaOH refers to sodium hydroxide; LiCl refers to lithium chloride; EtOH refers to ethanol; and LCAP refers to liquid chromatography area percent.

Example 1-1

Preparation of 2-fluoro-3-methylbenzeneboronic Acid (2)

This example demonstrates a process for preparing 2-fluoro-3-methylbenzeneboronic acid (i.e., a boronic acid) in accordance with an embodiment of the disclosure.

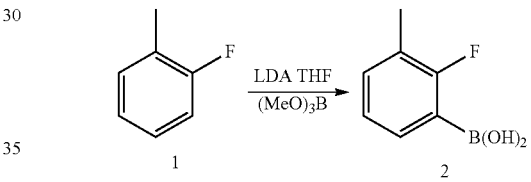

A 2 L four neck round bottom flask was charged with 320 mL of THF and 154.3 g of diisopropylamine. The resulting mixture was cooled to −15° C. and stirred. This was followed by addition of 582 mL of n-BuLi (2.5 M in n-hexane) dropwise under a nitrogen atmosphere while keeping the temperature below −10° C. After the addition was complete, the reaction was stirred for 30 min at −15° C. and then cooled to −35° C. This was followed by dropwise addition of a solution of 80 g of 2-fluorotoluene (1) in 160 mL of THF while the temperature was maintained below −30° C. The resulting mixture was subsequently stirred for 1 h at −35° C. This was followed by addition of 158.5 g of trimethyl borate to the reaction mixture while the temperature was maintained below −30° C. (exothermic reaction was observed). The reaction was stirred for 2 h at −35° C. and then allowed to warm to room temperature.

The reaction was then quenched by pouring onto an HCl solution of 658 g of water and 343 g of 30% HCl while maintaining the temperature at less than 30° C. The resulting mixture was extracted with MTBE (3×160 mL). The organic layers were combined and a solution of 1M NaOH/H₂O was added until pH>10. The water layer was then washed once with 160 mL of MTBE. To the water layer was added 240 mL of MTBE and a solution of 1M HCl until pH 1 in water layer. The water layer was then further extracted with MTBE (2×240 mL). The resulting organic layers were combined and washed once with 160 mL of water and then concentrated to provide 2 as a white powder which was used directly in the next reaction.

Example 1-2

Preparation of 2-fluoro-3-nitrotoluene (FNT) (3)

This example demonstrates a process for preparing FNT in accordance with an embodiment of the disclosure.

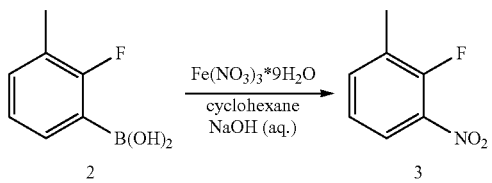

In a 1 L four necked round bottom flask, product 2, obtained from Example 1-1, was added to a mixture of 4 volumes of cyclohexane and 100 g (0.5 eq) of iron nitrate (Fe(NO$_3$)$_3$·9H$_2$O). The resulting reaction mixture was stirred at 65-75° C. for 12 hours. The reaction was monitored by HPLC until less than 5% of compound 2 was present, at which time the reaction was cooled to room temperature and filtered. The filter cake was washed with cyclohexane. The combined filtrate was then washed with 2×150 mL of 5% NaOH (aq.) and then 1×150 mL with water. The filtrate was concentrated and then distilled (e.g., 110-115° C. at 40-60 mmHg) to provide 38-42 g of FNT (3).

Example 2-1

Flow Preparation of 2-fluoro-3-methylbenzeneboronic Acid (2)

This example demonstrates a process for preparing 2-fluoro-3-methylbenzeneboronic acid (i.e., a boronic acid) in accordance with an embodiment of the disclosure.

A flow chemistry setup was as described in FIG. 1. Feed A (THF) and Feed B (DIPA) were connected via a T-mixer with relative flow rates as described below. A subsequent T-mixer connected the resulting stream with Feed C and lithiation occurs in a PFR with residence time of 5 min and bath temperature of −40 to −10° C. The resulting mixture was then passed into two sequential continuous stirred tank reactors (CSTRs) with residence time of 12-14 min each maintaining an internal temperature of −5 to 30° C. The resulting solution was collected under an atmosphere of nitrogen and represented a solution of approximately 1.5 M LDA in THF/hexanes (Table 1).

TABLE 1

LDA Preparation

| Feed | Reagent | Relative Flow (g/min) | Mass Flow (mL/min) | Relative Flow (mL/min) | Eqs. |
|---|---|---|---|---|---|
| A | THF | 1.207 | 1.36 | 1.00 | |
| B | DIPA | 1 | 1.39 | 1.03 | 1 |
| C | n-BuLi (2.5M) in hexanes | 2.814 | 4.06 | 2.99 | 1.03 |
| | Final LDA conc. (M) | | | 1.4896 | |

Figure 2:
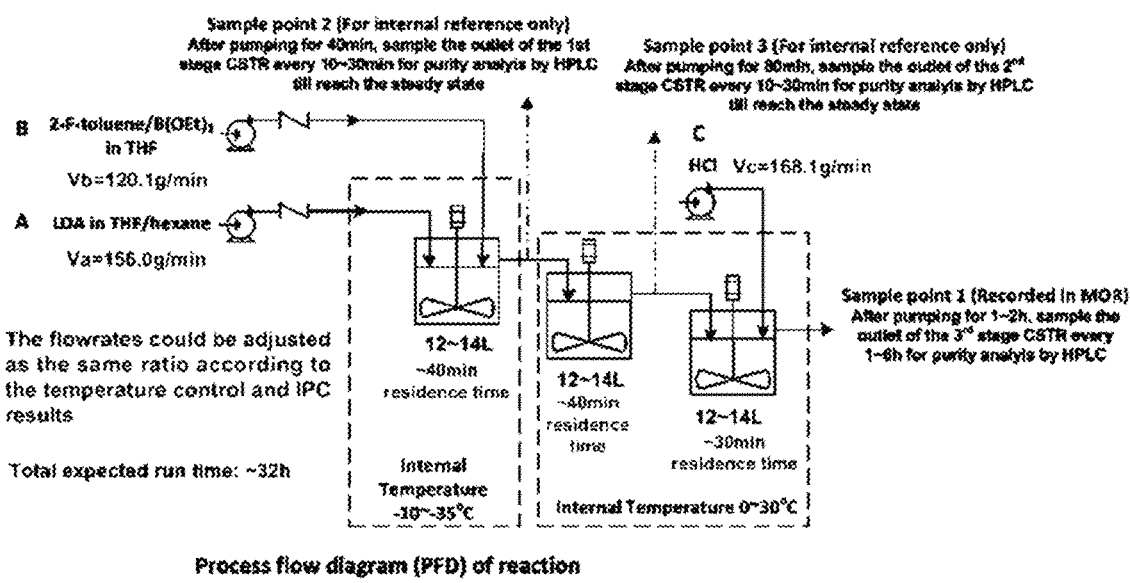
FIG. 2 shows the diagram for the set up for the flow chemistry borylation of 2-fluorotoluene in Example 2-1.

A flow chemistry setup for the borylation procedure was as illustrated in FIG. 2 under the conditions shown in Table 2. Feed A and Feed B were fed into a continuous stirred-tank reactor 1 (CSTR 1) (internal temp.=−10-35° C.) with a relative flow rate of 1:1.255 g/min (A:B) and a target residence time of approximately 40 min. Overflow from CSTR 1 fed into CSTR 2 (internal temp. 0-30° C., residence time of approximately 40 min) and finally into CSTR 3 (internal temp. 0-30° C., residence time=~30 min). Feed C was fed into CSTR 3 with a relative flow rate of 1.40 g/min.

TABLE 2

Borylation Procedure

| Feed | Reagent | Eqs. | Mass (kg/kg) | Volumes (L/kg) | Relative Flow (g/min) | Relative Flow (mL/min) | Eqs. |
|---|---|---|---|---|---|---|---|
| A | LDA from Step 1 | | | | 1.255 | density | 2.33 |
| B | 2-F-toluene | 1 | 1 | | 1 | density | 1 |
| | B(OEt)3 | 3.8 | 5.037 | 5.871 | | | |
| | THF | 6 vol | 5.32 | 6 | | | |
| C | HCl (36 wt %) | | 8.15 | 6.91 | 1.4 | density | 12.075 |
| | H$_2$O | | 15 | 15 | | | |
| | | | | Relative Ratio To (2) | | | |
| Output | Boric Acid | | | 2.8 | | | |
| | EtOH | | | 2.8 | | | |
| | DIPA | | | 2.33 | | | |
| | LiCl | | | 2.33 | | | |
| | THF | | | 6 vol | | | |
| | H$_2$O | | | 15 vol | | | |
| | HCl | | | 6 vol H$_2$O + 6 eq. HCl | | | |

Batch Isolation: The reaction mixture was quenched into 4 M aqueous HCl solution (15-20 vol.) below 30° C., the mixture was separated and the aqueous phase extracted with MTBE (3×5 volumes.). The organic phases were combined and the pH adjusted with 10% NaOH/H$_2$O until the pH was greater than 10. The aqueous phase was washed with MTBE (1×3 vol.). Then the aqueous phase was added with MTBE (5 vol.) and adjusted with 1 M HCl until pH=1-3. The obtained aqueous phase was extracted with MTBE (2×5 vol.). The organic phase was combined and washed once with water (3 vol.). The organic phase then was concentrated to 1-1.5 vol. and water (5 vol.) was added for crystallization and the reaction mixture cooled to 0-10° C. After stirring for 2 h, the mixture was filtrated and rinsed with water (2 vol.) The crude solid was slurried with heptane (3 vol.) for 1-3 h, then the mixture was filtrated and rinsed with heptane (1 vol.) The solid was dried with nitrogen below 35° C. to afford 2-fluorotoluene boronic acid as off-white or light yellow powder.

Example 2-2

Preparation of 2-fluoro-3-nitrotoluene (FNT) (3) via Nitric Acid

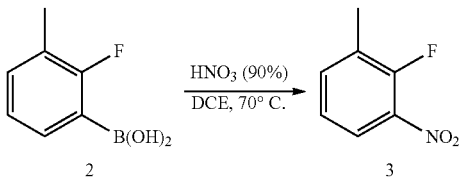

Reactor 1 was charged with 2-fluoro-3-methylbenzeneboronic acid (2). An NaOH scrubber was also fitted to reactor 1 to quench the release of $NO_2$ gas. 1,2-dichloroethane (10 vol.) was then added to reactor 1 at room temperature and agitation was started and the contents of the reaction were heated to 70° C. Once reactor 1 reached 70° C.±5° C. the reactor was charged with $HNO_3$ (fuming, 90%, 1.3 eq.). The reaction was then stirred at 70° C.±5° C. for 8 h.

The contents of the reaction were then allowed to cool to 20° C. Reactor 1 was then charged with water (10 vol.) and agitated for 30 min. The contents of reactor 1 were then polish filtered and the aqueous phase was discarded. An aqueous sodium bicarbonate solution (10 vol.) was then added and agitated for 30 min. and the aqueous phase was discarded. Another aqueous sodium bicarbonate solution (10 vol.) was then added and agitated for 30 min. and the aqueous phase was discarded. A solvent switch in the organic phase was then conducted from 1,2-dichloroethane to MeOH (8 vol.). Norix-SX1 Charcoal (2.5 wt %) was added and agitated for 2 hours. The contents of the reactor were filtered to remove charcoal and the filter was washed with MeOH (2 vol.). The contents of reactor 1 were cooled to 10° C. and water (5 vol.) was added over 3 h while maintaining the temperature at 10° C. The contents of reactor 1 were held at 10° C. for 30 min further and then cooled to 1 to 3° C. The solid contents of reactor 1 were then isolated by filtration and washed with 1:1 MeOH/water precooled to 3° C. The resulting solid was dried under vacuum at 3° C. for 16 h and 3 was isolated as a pale yellow solid.

Alternative Distillation Purification: 1,2-Dichloroethane is then removed by concentration under reduced pressure. The resulting brown oil was purified by distillation at 35 Torr. The product was distilled at 110-120° C. and the appropriate fractions were collected to afford a light green liquid which solidified to afford the product a white solid at room temperature.

Example 3

Flow Preparation of PIPN HBr from FNT

This example demonstrates a flow chemistry process in accordance with an embodiment of the disclosure.

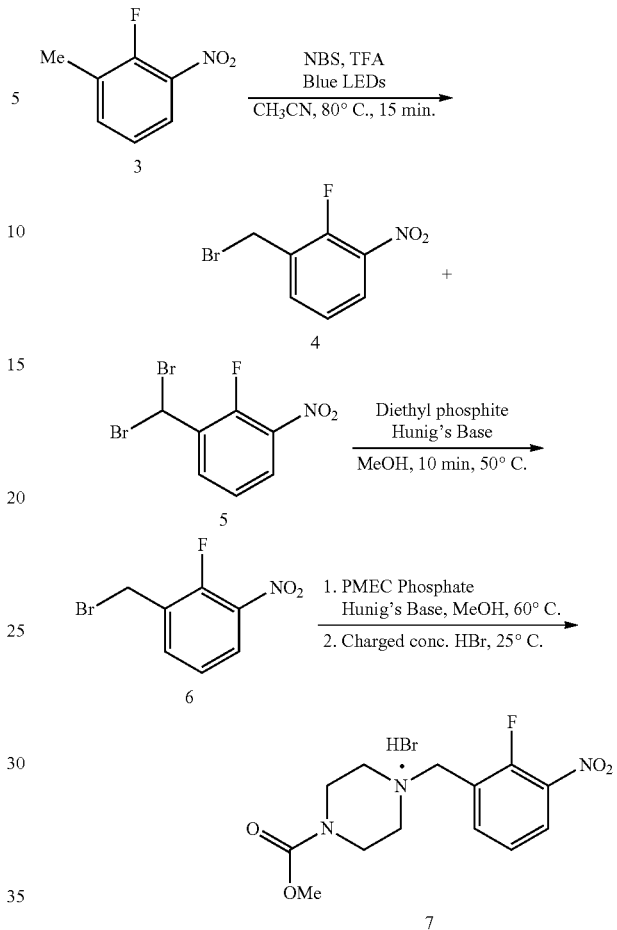

A FNT (3) stock solution was prepared by dissolving 100 g (647 mmol) FNT in 1087 mL of acetonitrile and 12 mL (161 mmol, 0.25 eq.) of trifluoroacetic acid. In the presence of blue LED light, NBS (143 g, 806 mmol, 1.25 eq.) was then added with stirring until the solution was homogenous.

A diethyl phosphite stock solution was prepared by dissolving 33 mL (258 mmol, 0.40 eq.) of diethyl phosphite in 100 mL of MeOH and 73 mL (418 mmol, 2.5 eq.) of N,N-diisopropylethylamine.

A PMEC phosphate stock solution was prepared by dissolving 144 g (648 mmol, 1.0 eq.) of PMEC phosphate in 300 mL of MeOH and 281 mL (1611 mmol, 2.5 eq.) of N,N-diisopropylethylamine. The thin slurry was then filtered, and the filter was rinsed with 100 mL of MeOH.

Figure 3:
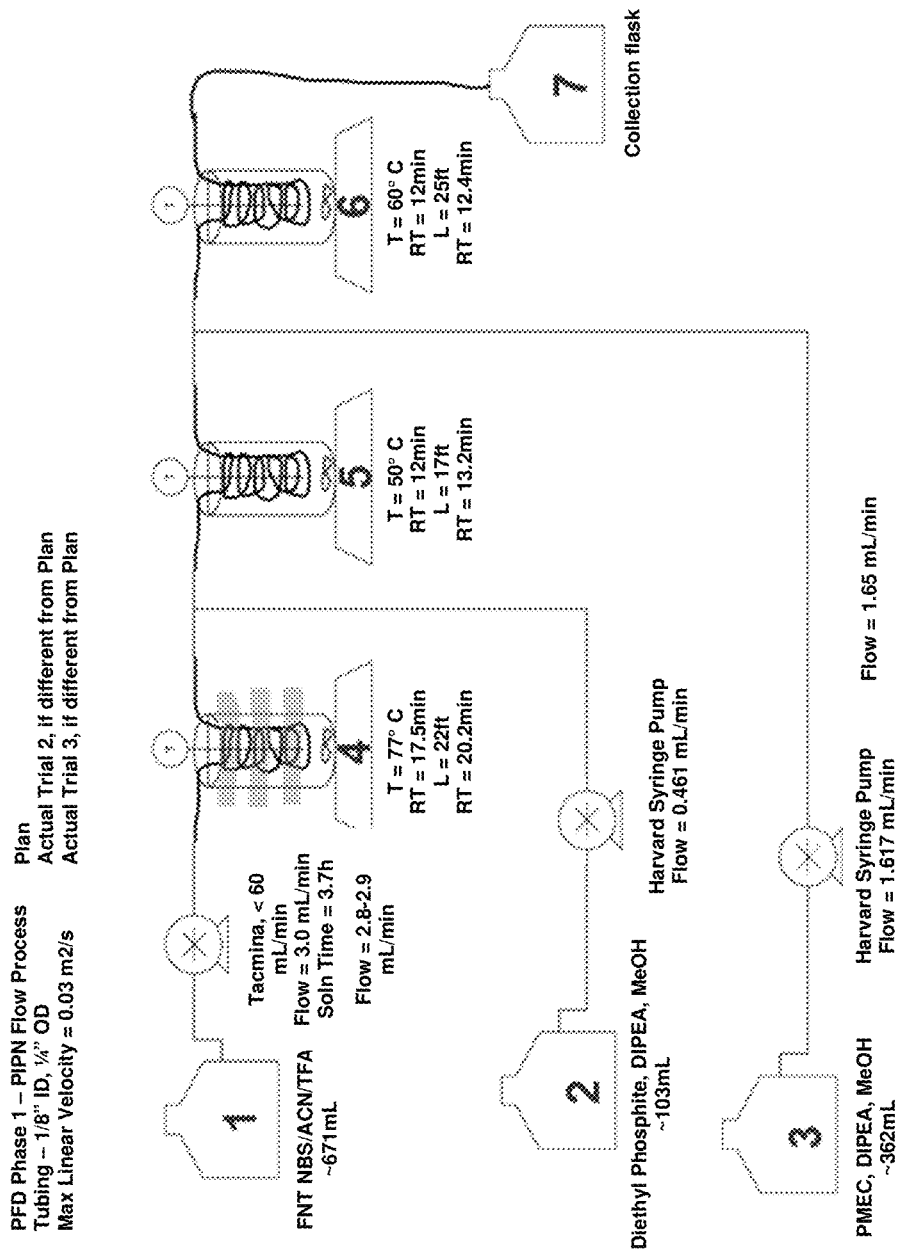
FIG. 3 provides a diagram for the setup of the flow chemistry preparation of PIPN HBr from FNT as described in Example 3.

The stock solutions were then pumped through a flow set up at a rate of 2.85 mL/min for the FNT solution, 0.46 mL/min for the diethyl phosphite solution, and 1.62 mL/min for the PMEC phosphate solution as shown in FIG. 3. All reaction loops were heated in thermostat-controlled water baths.

Figure 4:
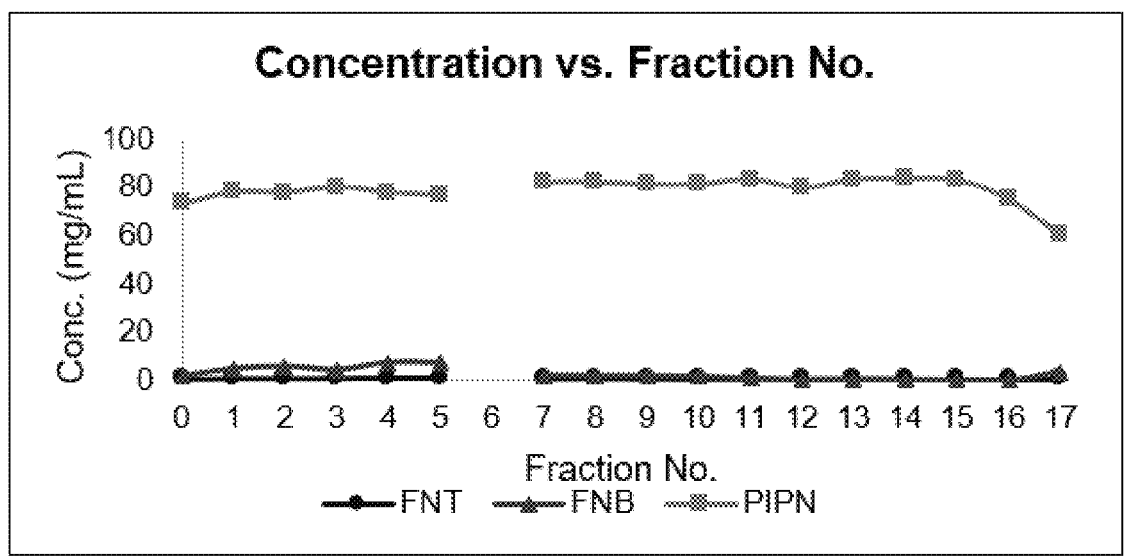
FIG. 4 shows a graph depicting the concentration data summary for the collected fractions for the crude PIPN stream from the flow chemistry preparation of PIPN HBr from FNT as described in Example 3.

The above set up was run for approximately 4 hours collecting fractions periodically along the way. The concentration data summary for the crude PIPN stream is shown in FIG. 4. Fractions 11-14 (~600 mL) was collected for crystallization.

For crystallization a seed bed was prepared by addition of 80 mL of acetonitrile and 1.39 g of PIPN HBr to a 2-L ChemGlass reactor and heated to 60° C. The crude PIPN solution was then added at an addition rate of 300 mL/h along with a concentrated HBr solution at 26 mL/h. After the addition was complete the slurry is held at 60° C. for 2 hours then cooled down to 25° C. over a period of 30 minutes and held at this temperature for an additional 60 minutes.

The slurry was then filtered and solids washed with 3×4 vol. acetonitrile at 55° C. The material was then dried under a nitrogen sweep. Recovered 53.55 g of PIPN HBr (76% yield), that was 99.9 LCAP and 97.3 wt % purity.

The foregoing examples are merely illustrative of embodiments of the disclosed processes described herein and are not intended to limit the disclosed methods. Variations and changes which are obvious to one skilled in the art are intended to be within the scope and nature of the disclosure which is defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing embodiments of the disclosure (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

What is claimed:

1. A process for synthesizing 2-fluoro-3-nitrotoluene ("FNT") comprising
    (a1) admixing 2-fluorotoluene with one or more bases and a boronation reagent to form a boronic acid; and
    (b1) admixing the resulting boronic acid with iron nitrate or a hydrate thereof to form the FNT;
    or
    (a2) admixing 2-fluorotoluene with one or more bases and a boronation reagent to form a boronic acid; and
    (b2) admixing the resulting boronic acid with nitric acid to form the FNT.

2. The process of claim 1, wherein the process comprises:
    (a1) admixing 2-fluorotoluene with one or more bases and a boronation reagent to form a boronic acid; and
    (b1) admixing the resulting boronic acid with iron nitrate or a hydrate thereof to form the FNT.

3. The process of claim 1, wherein the process comprises:
    (a2) admixing 2-fluorotoluene with one or more bases and a boronation reagent to form a boronic acid; and
    (b2) admixing the resulting boronic acid with nitric acid to form the FNT.

4. The process of claim 2, wherein step (a1) is carried out in a polar aprotic solvent.

5. The process of claim 4, wherein the polar aprotic solvent comprises tetrahydrofuran (THF).

6. The process of claim 2, wherein step (b1) is carried out in a non-polar solvent.

7. The process of claim 6, wherein the non-polar solvent comprises cyclohexane.

8. The process of claim 2, wherein the iron nitrate is hydrated.

9. The process of claim 8, wherein the iron nitrate has the formula, $Fe(NO_3)_3 \cdot 9H_2O$.

10. The process of claim 2, further comprising treating the product from step (b1) with a second base.

11. The process of claim 1, wherein the one or more bases comprises lithium diisopropylamide (LDA).

12. The process of claim 11, wherein the LDA is added in the presence of diisopropylamine (DIPA).

13. The process of claim 3, wherein step (a2) is carried out in a polar aprotic solvent.

14. The process of claim 13, wherein the polar aprotic solvent comprises tetrahydrofuran (THF).

15. The process of claim 3, wherein step (b2) is carried out in a polar aprotic solvent.

16. The process of claim 15, wherein the polar aprotic solvent comprises 1,2-dichloroethane (DCE).

17. The process of claim 16, wherein the DCE is present as 10 volumes to the boronation reagent.

18. The process of claim 3, wherein the nitric acid is 90% aqueous.

19. The process of claim 3, wherein the process further comprises heating the admixture formed in step (b2).

20. The process of claim 19, wherein the admixture is heated for no less than 8 hours.

21. The process of claim 19, wherein the admixture is heated to 70° C. for no less than 8 hours.

22. The process of claim 3, further comprising adding water to the admixture formed in step (b2).

23. The process of claim 22, wherein 10 volumes of water are added relative to the boronation reagent.

24. A process for synthesizing 1-(bromomethyl)-2-fluoro-3-nitrobenzene comprising

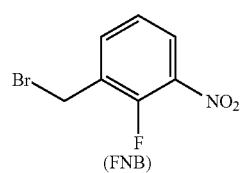
(FNB)

(a) admixing 2-fluoro-3-nitrotoluene (FNT) with a bromination agent in the presence of blue LED light to form a mixture of FNB and 1-(dibromomethyl)-2-fluoro-3-nitrobenzene

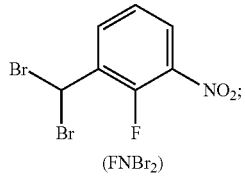

(FNBr₂)

(b) admixing the FNB/FNBr₂ mixture with a dialkyl phosphite to form FNB; and (c) optionally purifying FNB formed in step (b) by (i) washing the FNB with a dialkylphosphite and a trialkylamine, or (ii) extracting the FNB with an organic solvent and washing with aqueous base.

25. A process for synthesizing 1-(bromomethyl)-2-fluoro-3-nitrobenzene

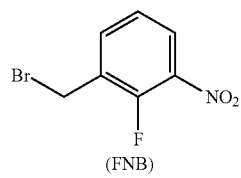

(FNB)

comprising (a) admixing the FNT prepared by the process of claim 1 with a bromination agent in the presence of blue LED light to form a mixture of FNB and 1-(dibromomethyl)-2-fluoro-3-nitrobenzene

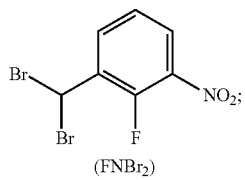

(FNBr₂)

(b) admixing the FNB/FNBr₂ mixture with a dialkyl phosphite to form FNB; and (c) optionally purifying FNB formed in step (b) by (i) washing the FNB with a dialkylphosphite and a trialkylamine, or (ii) extracting the FNB with an organic solvent and washing with aqueous base.

26. The process of claim 24, wherein the organic solvent is toluene.

27. The process of claim 24, wherein the base is sodium hydroxide.

28. The process of claim 24, wherein the bromination agent is selected from N-bromosuccinimide.

29. The process of claim 24, wherein the dialkyl phosphite is selected from the group consisting of dimethylphosphite, diethylphosphite, and a combination thereof.

30. The process of claim 24, further comprising (d) admixing the FNB, a trialkylamine base, and piperazine methyl carboxylate

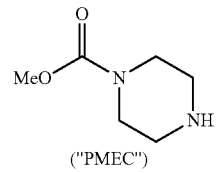

("PMEC")

phosphate hydrate to form methyl 4-(2-fluoro-3-nitrobenzyl)piperazine-1-carboxylate

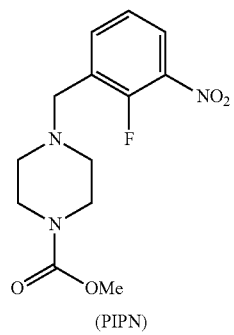

(PIPN)

or a salt thereof.

31. The process of claim 1, further comprising (c) admixing the FNT, benzoyl peroxide, N-bromosuccinimide, and acetic acid at a temperature of 70 to 95° C. to form 1-(bromomethyl)-2-fluoro-3-nitrobenzene

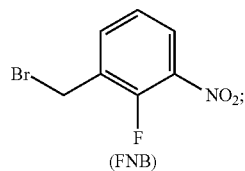

(FNB)

(d) optionally extracting FNB with toluene, washing FNB with an aqueous basic solution, or both;

(e) admixing FNB, a trialkylamine base, and piperazine methyl carboxylate

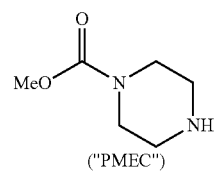

("PMEC")

phosphate hydrate to form methyl 4-(2-fluoro-3-nitrobenzyl)piperazine-1-carboxylate

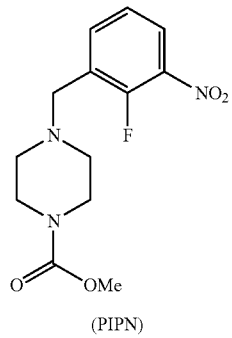
(PIPN)

or a salt thereof.

32. The process of claim 31, wherein FNB is extracted with toluene and washed with aqueous sodium hydroxide prior to step (e).

33. The process of claim 30, wherein the PIPN is formed as a hydrobromide salt.

34. The process of claim 30, wherein the PMEC phosphate hydrate is prepared by a process comprising
   (a) admixing piperazine and methyl chloroformate to form PMEC;
   (b) admixing the PMEC and 0.5 molar equivalents of phosphoric acid to form PMEC phosphate hydrate; and
   (c) optionally filtering the PMEC phosphate hydrate from the admixture of step (b).

35. The process of claim 34, further comprising isolating the PMEC formed from step (a) as a solution in a solvent selected from methylene chloride, dichloroethane, 2-methyltetrahydrofuran, and a mixture thereof.

36. The process of claim 35, wherein the isolating is performed by
   (i) washing the resulting PMEC from step (a) with an organic solvent;
   (ii) modifying the pH to 8 to 14 by adding a base to form a basic aqueous solution; and
   (iii) extracting the PMEC from the basic aqueous solution of step (ii) with methylene chloride, dichloroethane, 2-methyl tetrahydrofuran, or a mixture thereof.

37. The process of claim 34, wherein step (a) is performed in an aqueous solution.

38. The process of claim 34, wherein step (a) is performed at a temperature of 20 to 55° C. for 1 to 12 hours.

39. The process of claim 30, wherein the trialkylamine base comprises diisopropylethylamine or triethylamine.

40. The process of claim 30, wherein prior to admixing the FNB, the trialkylamine base, and the PMEC phosphate hydrate, the process further comprises adding diethylphosphite and a trialkylamine base, and admixing the resulting mixture at a temperature of 30 to 65° C.

41. The process of claim 30, further comprising
   (f) admixing the PIPN or salt thereof, an aqueous solution of an inorganic base, and toluene to form a PIPN freebase solution;
   (g) hydrogenating the PIPN freebase solution in the presence of a palladium catalyst in a solvent comprising toluene and alcohol to form crude methyl 4-(3-amino-2-fluorobenzyl)piperazine-1-carboxylate (PIPA):

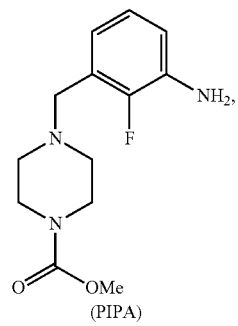 [SMILES: COC(=O)N1CCN(Cc2cccc(N)c2F)CC1]
(PIPA)

wherein the alcohol comprises ethanol or isopropanol; and
   (h) crystallizing the PIPA from the crude PIPA in heptane and toluene.

42. The process of claim 41, wherein the inorganic base comprises sodium hydroxide.

43. The process of claim 41, further comprising
   (i) admixing the PIPA, phenyl (6-methylpyridin-3-yl) carbamate

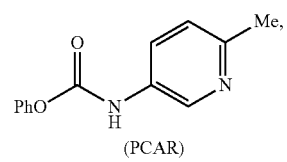 [SMILES: Cc1ccc(NC(=O)Oc2ccccc2)cn1]
(PCAR)

and a trialkylamine base in acetonitrile and tetrahydrofuran to form a solution of crude omecamtiv mecarbil; and
   (j) isolating omecamtiv mecarbil free base from the solution of crude omecamtiv mecarbil.

44. The process of claim 43, wherein the trialkylamine base comprises diisopropylethylamine or triethylamine.

45. The process of claim 43, wherein the isolating of step (j)(h) comprises crystallizing omecamtiv mecarbil free base by adding water to the solution of crude omecamtiv mecarbil from step (i) and filtering the crystallized omecamtiv mecarbil free base.

46. The process of claim 43, further comprising crystallizing the omecamtiv mecarbil dihydrochloride hydrate from isopropanol and water.

47. The process of claim 43, wherein the PCAR or a salt thereof is prepared by a process comprising admixing 5-amino-2-methylpyridine

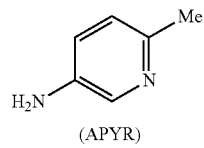
(APYR)

and phenyl chloroformate in acetonitrile to form PCAR or a salt thereof, wherein the admixing is performed in the absence of N-methyl 2-pyrrolidinone (NMP).

48. The process of claim 47, wherein the admixing is performed at a temperature of 15 to 30° C. for 1 to 15 hours.

49. The process of claim 47, wherein the PCAR is formed as a hydrochloride salt.

50. The process of claim 47, wherein the APYR is prepared by a process comprising (i) hydrogenating 2-methyl-5-nitropyridine

(NPYR)

in the presence of a palladium catalyst to form crude APYR; and
(ii) crystallizing the crude from isopropyl acetate and heptane.

51. The process of claim 50, further comprising, prior to step (i), washing NPYR in isopropyl acetate with aqueous sodium hydroxide, followed by admixing the washed NPYR in isopropyl acetate with charcoal.

52. The process of claim 47, further comprising, prior to admixing APYR and phenyl chloroformate, purifying APYR by a process comprising:
(i) washing an isopropyl acetate solution of crude APYR, wherein the crude APYR comprises up to 10 wt % APYR hydrochloride, with aqueous sodium hydroxide, and admixing the washed APYR with charcoal to form an APYR solution after filtration; and
(ii) crystallizing APYR from the APYR solution of step (i) from isopropyl acetate and heptane.

53. The process of claim 47, further comprising crystallizing PCAR.

54. The process of claim 41, further comprising
(i) admixing the PIPA, triphosgene, and a trialkylamine in acetonitrile and tetrahydrofuran to form PIPA isocyanate;
(j) admixing the PIPA isocyanate and 5-amino-2-methylpyridine

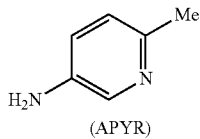

(APYR)

to form omecamtiv mecarbil free base; and
(k) admixing the omecamtiv mecarbil free base with 2 to 3 molar equivalents of hydrochloric acid in isopropanol and water to form omecamtiv mecarbil dihydrochloride hydrate.

55. The process of claim 54, wherein step (i) is performed via continuous manufacturing comprising admixing a first solution comprising PIPA and the trialkylamine in acetonitrile and a second solution comprising triphosgene in tetrahydrofuran using a micromixer chip and a reaction loop to form the PIPA isocyanate.

56. The process of claim 54, wherein step (j) is performed via continuous manufacturing comprising admixing a solution comprising the PIPA isocyanate and a solution comprising the AYPR using a Y-mixer and a reaction loop.

57. A process for preparing omecamtiv mecarbil or a salt thereof, a hydrate thereof, or a salt hydrate thereof, the process comprising the process of claim 1.

58. The process of claim 57, wherein the omecamtiv mecarbil, salt thereof, hydrate thereof, or salt hydrate thereof is omecamtiv mecarbil dihydrochloride hydrate.

59. The process of claim 43, further comprising admixing the isolated omecamtiv mecarbil free base from step (j) with 2 to 3 molar equivalents of hydrochloric acid in isopropanol and water to form omecamtiv mecarbil dihydrochloride hydrate

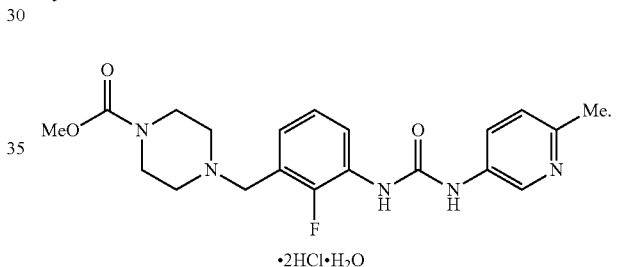

·2HCl·H$_2$O

* * * * *

UNITED STATES PATENT AND TRADEMARK OFFICE
CERTIFICATE OF CORRECTION

PATENT NO. : 11,702,380 B2
APPLICATION NO. : 17/690729
DATED : July 18, 2023
INVENTOR(S) : Sebastien Caille et al.

Page 1 of 1

It is certified that error appears in the above-identified patent and that said Letters Patent is hereby corrected as shown below:

In the Claims

In Claim 45, at Column 34, Line number 40, please replace "(j)(h)" with -- (j) --

In Claim 56, at Column 36, Line number 16, please replace "AYPR" with -- APYR --

Signed and Sealed this
Eighth Day of April, 2025

Coke Morgan Stewart
*Acting Director of the United States Patent and Trademark Office*